(12) United States Patent
Jorgensen et al.

(10) Patent No.: US 10,463,363 B2
(45) Date of Patent: Nov. 5, 2019

(54) SUTURE PASSER

(71) Applicant: Quantum Medical Innovations, LLC, Jacksonville, FL (US)

(72) Inventors: Glen Jorgensen, Jacksonville, FL (US); Steven Reeser, Jacksonville, FL (US); Bruce Ramshaw, Jacksonville, FL (US)

(73) Assignee: Quantum Medical Innovations LLC, Jacksonville, FL (US)

( * ) Notice: Subject to any disclaimer, the term of this patent is extended or adjusted under 35 U.S.C. 154(b) by 597 days.

(21) Appl. No.: 14/681,789

(22) Filed: Apr. 8, 2015

(65) Prior Publication Data
US 2015/0282806 A1 Oct. 8, 2015

Related U.S. Application Data

(60) Provisional application No. 61/976,842, filed on Apr. 8, 2014.

(51) Int. Cl.
*A61B 17/04* (2006.01)
*A61B 17/06* (2006.01)
*A61B 17/00* (2006.01)

(52) U.S. Cl.
CPC ...... *A61B 17/0485* (2013.01); *A61B 17/0469* (2013.01); *A61B 17/0482* (2013.01); *A61B 2017/00358* (2013.01); *A61B 2017/00986* (2013.01); *A61B 2017/0472* (2013.01); *A61B 2017/06052* (2013.01)

(58) Field of Classification Search
CPC .......... A61B 17/0469; A61B 17/0482; A61B 17/0485; A61B 2017/0472; A61B 17/04; A61B 17/34; A61B 17/3403; A61B 2017/3405; A61B 2017/3445
See application file for complete search history.

(56) References Cited

U.S. PATENT DOCUMENTS

| 7,918,868 | B2 | 4/2011 | Marshall et al. | |
|---|---|---|---|---|
| 2001/0044638 | A1* | 11/2001 | Levinson | A61B 17/0057 606/228 |
| 2005/0121042 | A1* | 6/2005 | Belhe | A61B 17/0057 128/887 |
| 2006/0069398 | A1* | 3/2006 | Suzuki | A61B 17/0482 606/148 |

(Continued)

FOREIGN PATENT DOCUMENTS

| WO | WO 2007/138981 | 12/2007 |
|---|---|---|
| WO | WO 2009/113222 | 9/2009 |

*Primary Examiner* — Ryan J. Severson
*Assistant Examiner* — Christian D Knauss
(74) *Attorney, Agent, or Firm* — Pandiscio & Pandiscio

(57) ABSTRACT

A suture passer comprising: a handle; a first needle mounted to the handle; a retrieving loop selectively extendable out of, and selectively retractable into, the first needle; a second needle mounted to the handle, the second needle being configured to pass suture therethrough; a housing having first and second lumens extending therethrough for receiving the first and second needles therein, respectively; wherein the suture passer is configured so that the first and second needles have (i) a first distance therebetween at the location at which the first and second needles pass through the housing, and (ii) a second distance therebetween at a location remote from the housing, and further wherein the second distance is greater than the first distance.

9 Claims, 15 Drawing Sheets

(56) References Cited

U.S. PATENT DOCUMENTS

| | | | |
|---|---|---|---|
| 2008/0065120 A1* | 3/2008 | Zannis | A61B 17/0401 606/144 |
| 2009/0062817 A1* | 3/2009 | Suzuki | A61B 17/0482 606/144 |
| 2009/0264905 A1* | 10/2009 | Funada | A61B 17/04 606/146 |
| 2009/0264906 A1 | 10/2009 | McDonnell | |
| 2011/0245850 A1* | 10/2011 | van der Burg | A61B 17/0401 606/145 |
| 2013/0116708 A1* | 5/2013 | Ziniti | A61B 17/0485 606/144 |

\* cited by examiner

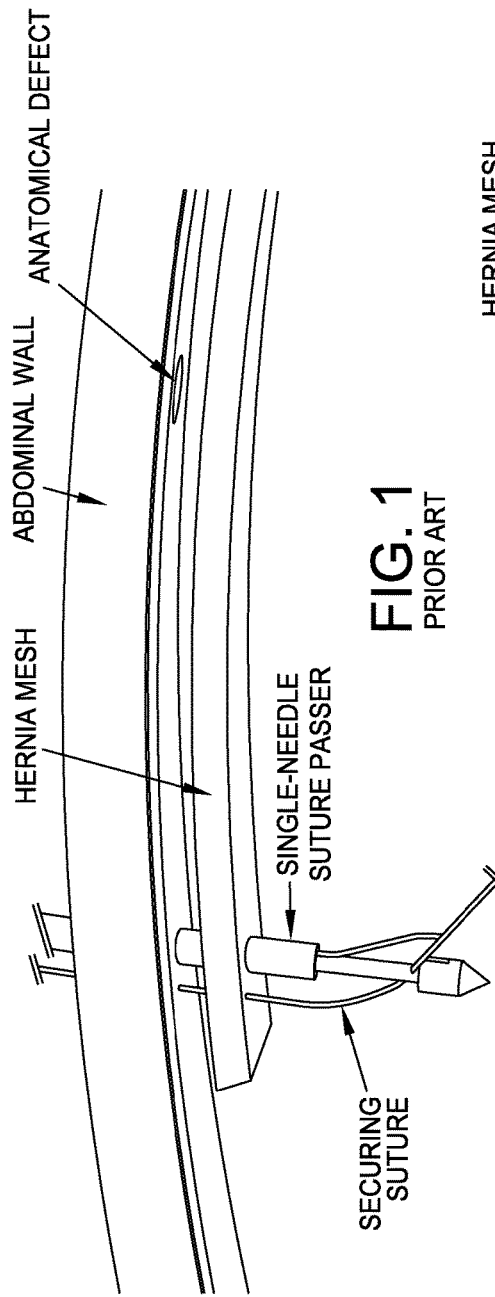
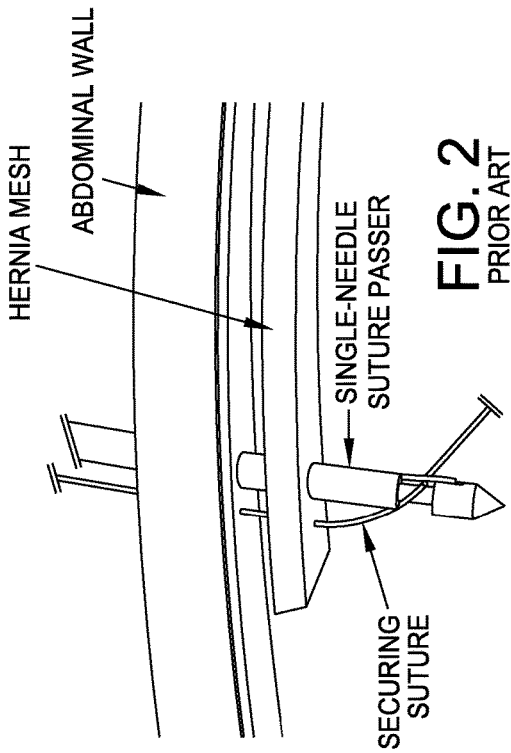
FIG. 1 PRIOR ART
FIG. 2 PRIOR ART

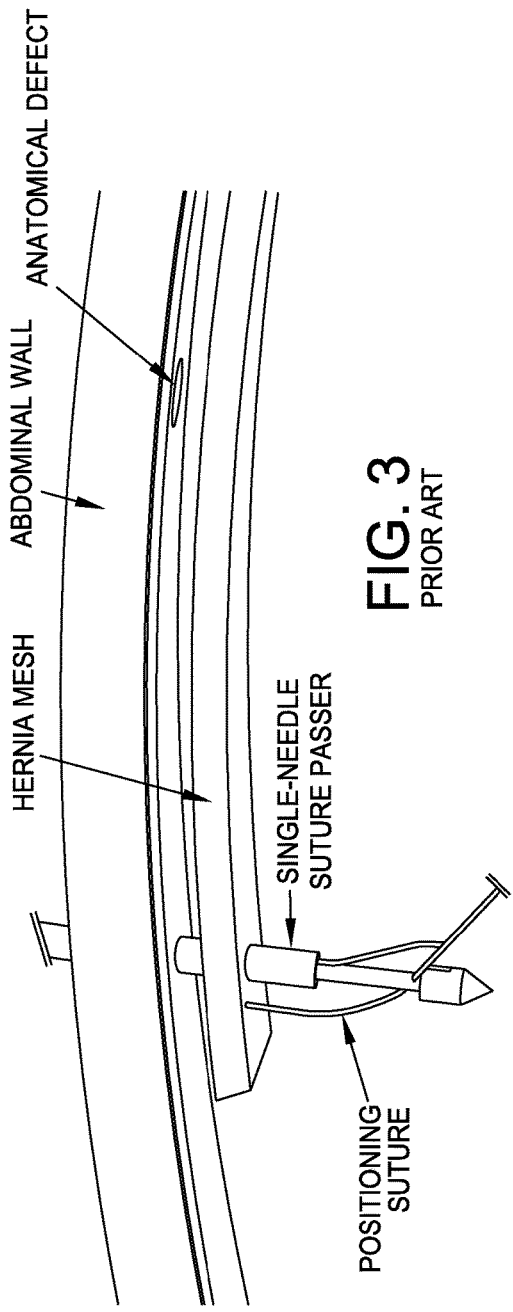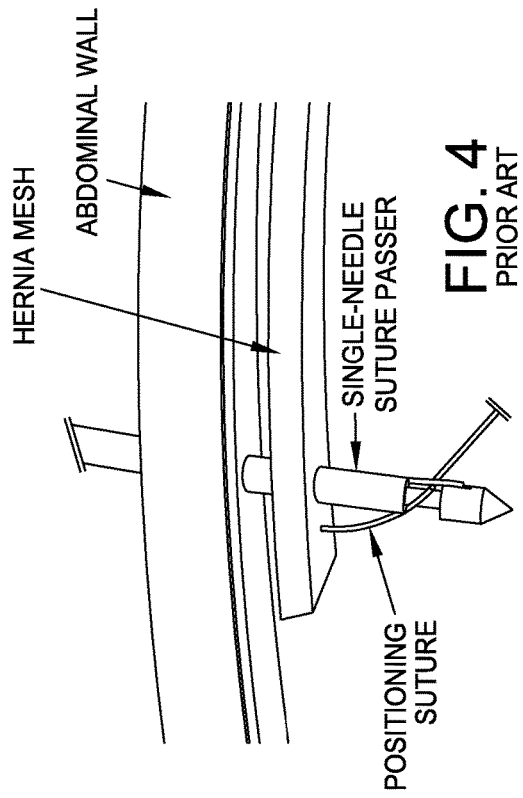
FIG. 3
PRIOR ART
FIG. 4
PRIOR ART

SUTURE PASSER

REFERENCE TO PENDING PRIOR PATENT APPLICATION

This patent application claims benefit of prior U.S. Provisional Patent Application Ser. No. 61/976,842, filed Apr. 8, 2014 by Quantum Medical Innovations, LLC and Glen Jorgensen et al. for SUTURE PASSER, which patent application is hereby incorporated herein by reference.

FIELD OF THE INVENTION

This invention relates to surgical apparatus and methods in general, and more particularly to surgical apparatus and methods for passing suture.

BACKGROUND OF THE INVENTION

A hernia occurs when part of an internal organ, most often the intestines, protrudes through an abnormal opening or weakening in the wall surrounding the abdominal cavity.

There are four main types of abdominal hernias: (1) Inguinal Hernia—a bulge in the groin; (2) Femoral or Ventral Hernia—a bulge in the groin that appears between the navel and the breastbone; (3) Umbilical Hernia (newborn-related or paraumbilical hernia)—a bulge in the navel area; and (4) Incisional Hernia—a bulge in the stomach and navel area that is usually caused by a prior surgical incision in the area. A hernia is called reducible if the bulge can be manipulated back into place inside the abdomen. A hernia is called irreducible or incarcerated when the hernia cannot be reduced, e.g., because adhesions have formed in the internal sac. A hernia is characterized as strangulated if part of the herniated intestine becomes twisted or edematous (swollen), causing serious complications.

Hernia repairs are sometimes subdivided into two classes, laparoscopic repair and open repair, both of which are accomplished by strengthening the defect with a synthetic hernia mesh. In the case of open repair, an incision is made in the vicinity of the defect to expose the defect area such that the hernia mesh can be attached to surrounding tissue (e.g., with sutures and/or tacks). In the case of laparoscopic repair, instruments and internal cameras specially designed for the intricate procedure make minimally invasive internal repair possible. Laparoscopic repair typically involves inserting the hernia mesh into the abdominal cavity through a small instrument port (sometimes referred to as an access cannula or a trocar) and then attaching the hernia mesh to the distal side of the defect with sutures and/or tacks, whereby to strengthen the defect. This type of hernia repair typically results in less pain for the patient and faster recovery times.

Fixation of the hernia mesh over the defect is required for both open repair and laparoscopic repair in order to avoid postoperative migration of the hernia mesh. Fixation of the hernia mesh to the abdominal wall is generally accomplished using sutures and/or tacks.

Currently, single-needle suture passers are generally used to pass sutures through the abdominal wall and the hernia mesh. These single-needle suture passers typically comprise a hook-and-clasp piercing tip that releasably secures the suture to the needle with a clasping detail that opens as the hook-and-clasp piercing tip is extended distally from the needle and closes when the hook-and-clasp piercing tip is withdrawn back into the needle. See FIGS. 1 and 2.

For each suture (typically referred to as a "securing suture"), the abdominal cavity is pierced twice: (1) the first time at a first location to pass (antegrade) a first end of a securing suture from outside the body, through the abdominal wall, through the hernia mesh, and then release the first end of the securing suture within the abdominal cavity; and (2) the second time at a second, laterally-spaced location to retrieve the first end of the securing suture and to pass it (retrograde) back through the hernia mesh and abdominal wall to a point outside the body. By laterally spacing the location of the second needle penetration from the location of the first needle penetration, a portion of the securing suture will extend along a portion of the hernia mesh so as to securely engage the hernia mesh. The surgeon then ties the first end of the securing suture to a second end of the securing suture, thereby securing the hernia mesh to the abdominal wall.

In some cases the hernia mesh may be "pre-equipped" with one or more "positioning sutures", wherein the positioning sutures have been secured to the hernia mesh prior to the hernia mesh being inserted into the abdominal cavity. In this situation, after the hernia mesh has been positioned inside the abdominal cavity, a single-needle suture passer is passed (antegrade) from the region outside the body through the abdominal wall and through the hernia mesh, then the suture passer is used to grasp the free end of the positioning suture (see FIGS. 3 and 4) and pull it back through the hernia mesh and the abdominal wall, so that the surgeon may thereafter use the positioning suture to hold the hernia mesh in position against the abdominal wall while securing sutures are set and tied down in the manner previously described.

Improvements are needed to eliminate the time required for the aforementioned double-piercing operation when setting securing sutures using single-needle suture passers, and for ensuring the accurate placement of the first and second needle penetrations by the single-needle suture passers so as to facilitate proper positioning of the securing sutures. These improvements include the use of a twin-needle, single-penetration approach that employs a twin-needle suture passer having a first needle to pass the securing suture into the abdominal cavity and a second needle to retrieve the securing suture from the abdominal cavity. However, the twin-needle suture passers developed to date tend to suffer from a variety of limitations.

To be more broadly accepted, (i) the twin needles should enter the abdominal cavity through a small (e.g., 3 mm) incision and then controlled to open to a larger spread (e.g., 10 mm) as the needles pass through the hernia mesh; (ii) the device should be easily reloaded with multiple securing sutures throughout the procedure; (iii) the device should be easily adaptable from a twin-needle suture passer for deploying multiple securing sutures to a single-needle suture retriever for grasping the loose ends of positioning sutures and pulling them back through the hernia mesh and the abdominal wall; and (iv) the device should include an added safety feature to cover the sharp tips of the needles until the sharp tips are disposed in the abdomen, whereby to protect medical personnel as the device is passed to and from the surgeon.

SUMMARY OF THE INVENTION

The present invention comprises the provision and use of a novel twin-needle, single-penetration approach that employs a twin-needle suture passer having a first needle to pass suture into the abdominal cavity and a second needle to retrieve suture from the abdominal cavity. In accordance with the present invention, (i) the twin needles are configured to enter the abdominal cavity through a small (e.g., 3 mm) incision and then controlled to open to a larger spread (e.g., 10 mm) as the needles pass through the hernia mesh; (ii) the device is easily reloaded with multiple securing sutures throughout the procedure; (iii) the device is easily adaptable from a twin-needle suture passer for deploying multiple securing sutures to a single-needle suture retriever for grasping the loose ends of positioning sutures and pulling them back through the hernia mesh and the abdominal wall; and (iv) the device includes an added safety feature to cover the sharp tips of the needles until the sharp tips are disposed in the abdomen, whereby to protect medical personnel as the device is passed to and from the surgeon.

In one preferred form of the invention, there is provided a twin-needle suture passer configured to pass suture through at least one object by passing a first end of a suture through a first needle which has been passed through the at least one object and then passing the first end of the suture through a pre-formed loop that selectively slidably protrudes from a second needle which has been passed through the at least one object, wherein withdrawing the pre-formed loop back into the second needle after the first end of the suture has been passed through the pre-formed loop captures the first end of the suture to the second needle, such that when both needles are withdrawn back through the at least one object, the first end of the suture is withdrawn back through the at least one object and is positioned to be joined to a second end of the suture, wherein the first and second needles are configured, and passed through a housing, such that the first and second needles have (i) a first distance therebetween at the location at which the first and second needles pass through the at least one object, and (ii) a second distance therebetween at the location at which the first end of the suture passes through the pre-formed loop, and further wherein the second distance is greater than the first distance.

In another preferred form of the invention, there is provided a method for passing suture, the method comprising:

providing a twin-needle suture passer configured to pass suture through at least one object by passing a first end of a suture through a first needle which has been passed through the at least one object and then passing the first end of the suture through a pre-formed loop that selectively slidably protrudes from a second needle which has been passed through the at least one object, wherein withdrawing the pre-formed loop back into the second needle after the first end of the suture has been passed through the pre-formed loop captures the first end of the suture to the second needle, such that when both needles are withdrawn back through the at least one object, the first end of the suture is withdrawn back through the at least one object and is positioned to be joined to a second end of the suture, wherein the first and second needles are configured, and passed through a housing, so that the first and second needles have (i) a first distance therebetween at the location at which the first and second needles pass through the at least one object, and (ii) a second distance therebetween at the location at which the first end of the suture passes through the pre-formed loop, and further wherein the second distance is greater than the first distance;

passing at least the second needle through the at least one object, extending the pre-formed loop out of the second needle, and passing the first end of the suture through the pre-formed loop;

retracting the pre-formed loop into the second needle; and
retracting the second needle from the at least one object.

In another preferred form of the invention, there is provided a suture passer comprising:

a handle;
a first needle mounted to the handle;
a retrieving loop selectively extendable out of, and selectively retractable into, the first needle;
a second needle mounted to the handle, the second needle being configured to pass suture therethrough;
a housing having first and second lumens extending therethrough for receiving the first and second needles therein, respectively;
wherein the suture passer is configured so that the first and second needles have (i) a first distance therebetween at the location at which the first and second needles pass through the housing, and (ii) a second distance therebetween at a location remote from the housing, and further wherein the second distance is greater than the first distance.

In another preferred form of the invention, there is provided a method for passing suture, the method comprising:

providing a suture passer comprising:
a handle;
a first needle mounted to the handle;
a retrieving loop selectively extendable out of, and selectively retractable into, the first needle;
a second needle mounted to the handle, the second needle being configured to pass suture therethrough;
a housing having first and second lumens extending therethrough for receiving the first and second needles therein, respectively;
wherein the suture passer is configured so that the first and second needles have (i) a first distance therebetween at the location at which the first and second needles pass through the housing, and (ii) a second distance therebetween at a location remote from the housing, and further wherein the second distance is greater than the first distance;

passing the first needle through at least one object, extending the retrieving loop out of the first needle, and passing the first end of the suture through the retrieving loop;
retracting the retrieving loop into the first needle; and
retracting the first needle from the at least one object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 1 and 2 are schematic views showing a prior art single-needle suture passer retrieving a securing suture in the course of a hernia repair procedure;

FIGS. 3 and 4 are schematic views showing a prior art single-needle suture passer retrieving a positioning suture in the course of a hernia repair procedure;

DETAILED DESCRIPTION OF THE PREFERRED EMBODIMENTS

Figure 5:
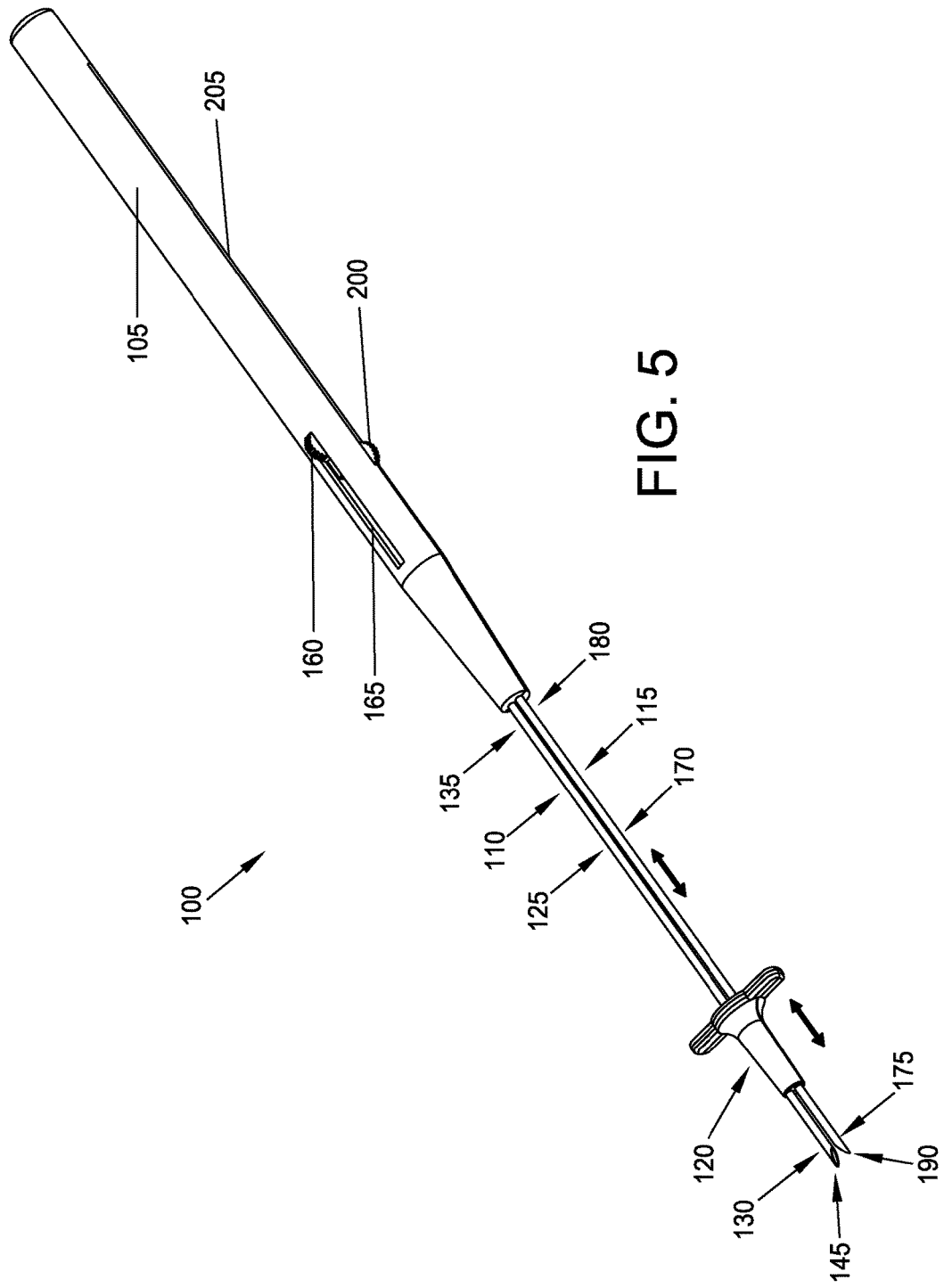
FIGS. 5-8 are schematic views showing a novel suture passer formed in accordance with the present invention.
Figure 6:
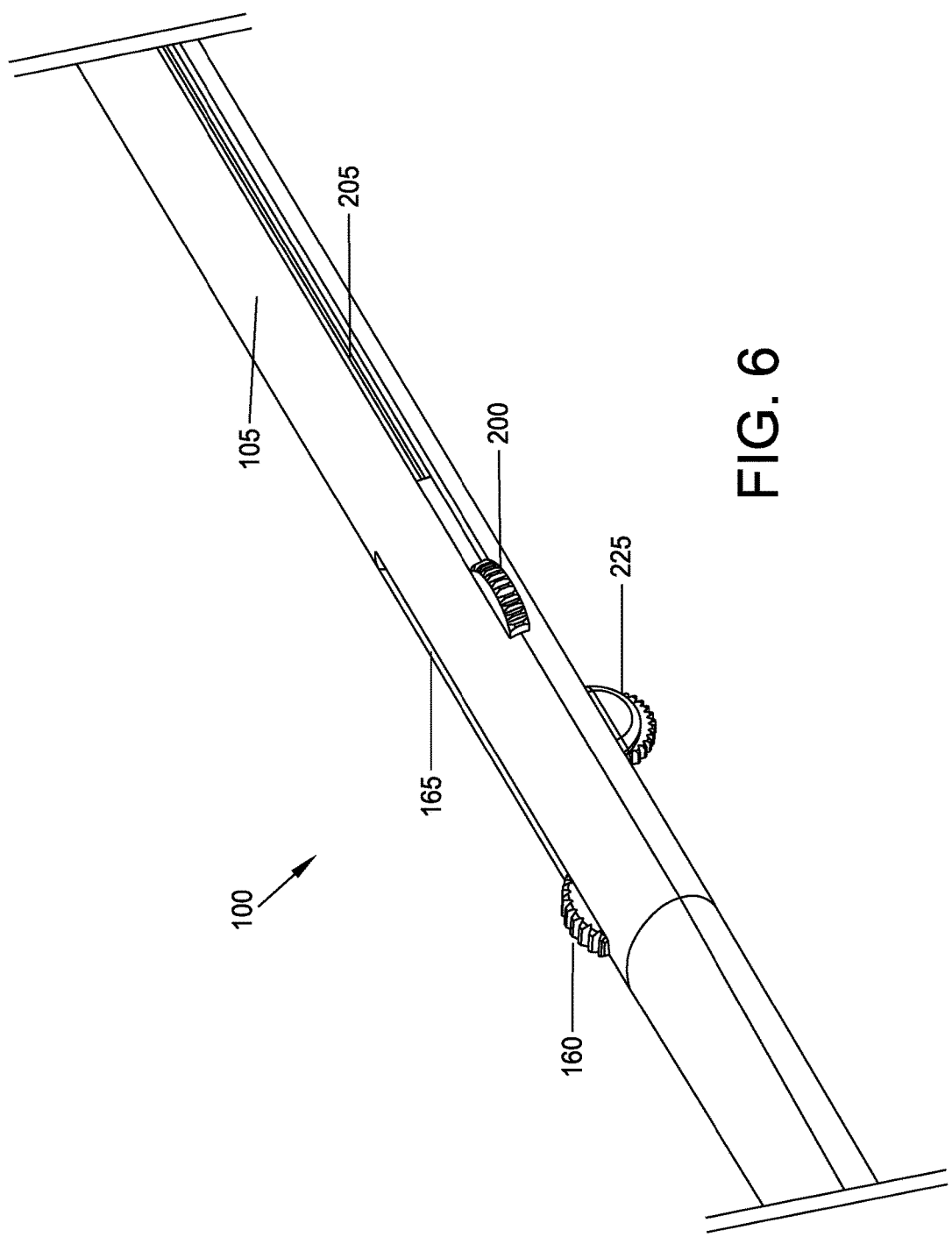
Figure 7:
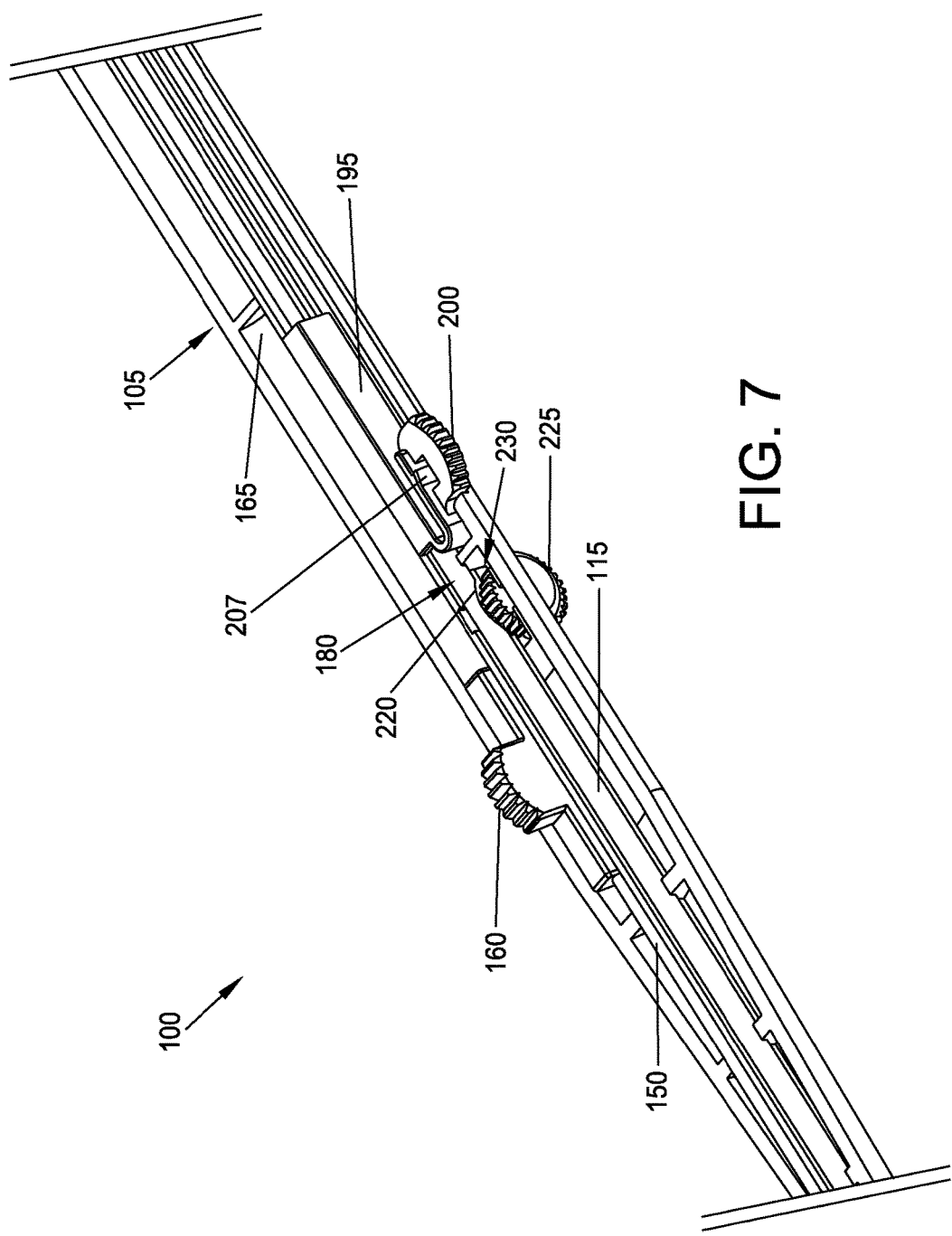

The present invention comprises the provision and use of a novel twin-needle, single-penetration approach that employs a twin-needle suture passer having a first needle to pass suture into the abdominal cavity and a second needle to retrieve suture from the abdominal cavity. In accordance with the present invention, (i) the twin needles are configured to enter the abdominal cavity through a small (e.g., 3 mm) incision and then controlled to open to a larger spread (e.g., 10 mm) as the needles pass through the hernia mesh; (ii) the device is easily reloaded with multiple securing sutures throughout the procedure; (iii) the device is easily adaptable from a twin-needle suture passer for deploying multiple securing sutures to a single-needle suture retriever for grasping the loose ends of the positioning sutures and pulling them back through the hernia mesh and the abdominal wall; and (iv) the device includes an added safety feature to cover the sharp tips of the needles until the sharp tips are disposed in the abdomen, whereby to protect medical personnel as the device is passed to and from the surgeon.

Looking first at FIGS. 5-8, there is shown a suture passer 100 formed in accordance with the present invention. Suture passer 100 generally comprises a handle 105, a retrieving needle 110 fixedly mounted to handle 105, a suture needle 115 movably mounted to handle 105, and a nose cone 120 movably mounted on retrieving needle 110 and suture needle 115.

Retrieving needle 110 comprises a shaft 125 having a distal end 130, a proximal end 135 and a lumen 140 (FIGS. 11 and 16) extending therethrough. Distal end 130 of retrieving needle 110 terminates in a sharp distal tip 145. Proximal end 135 of retrieving needle 110 is secured to handle 105. A retrieving shaft 150 (FIGS. 7, 11 and 16) is movably mounted in lumen 140 of retrieving needle 110. A retrieving loop 155 (FIGS. 10, 11, 15 and 16) is secured to the distal end of retrieving shaft 150. Retrieving loop 155 preferably comprises a loop end 157 (FIGS. 11 and 16) having a generous radius which mitigates stress cracking during repeated flexing throughout the repair procedure and which provides a shape detail into which the securing suture/positioning suture can be secured, as will hereinafter be discussed in greater detail. A retrieving knob 160 is secured to the proximal end of retrieving shaft 150. Retrieving knob 160 rides in a retrieving knob slot 165 formed in handle 105. On account of the foregoing construction, distal movement of retrieving knob 160 in retrieving knob slot 165 causes retrieving shaft 150 to move distally in lumen 140 of retrieving needle 110 so that retrieving loop 155 projects out the distal end 130 of retrieving needle 110 (FIGS. 10, 11, 15 and 16), and proximal movement of retrieving knob 160 in retrieving knob slot 165 causes retrieving shaft 150 to move proximally in lumen 140 of retrieving needle 110 so that retrieving loop 155 is retracted into the distal end 130 of retrieving needle 110 (FIGS. 5, 9 and 12-14).

Figure 9:
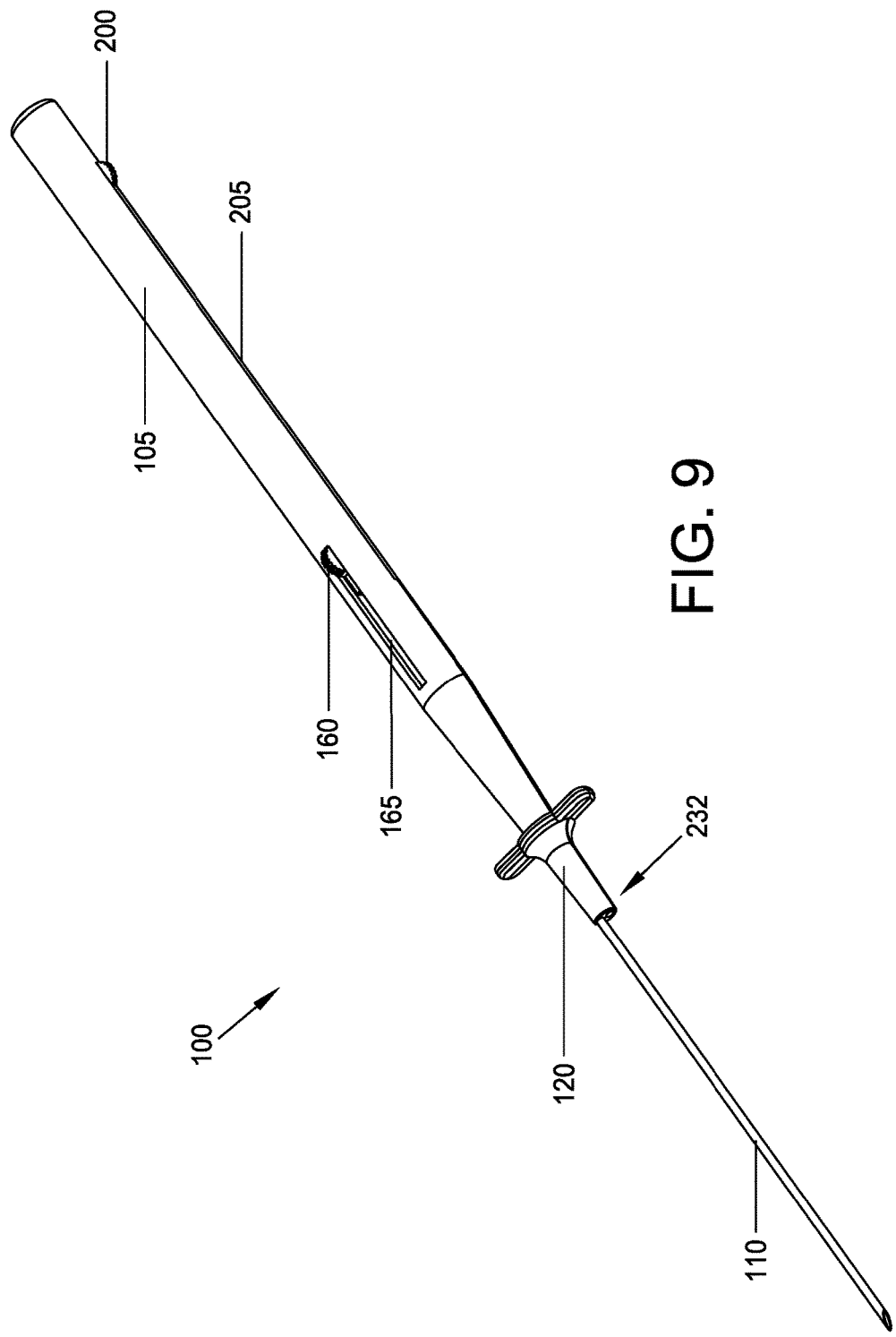
FIGS. 9-11 are schematic views showing the novel suture passer of FIGS. 5-8 being used to retrieve a positioning suture.
Figure 10:
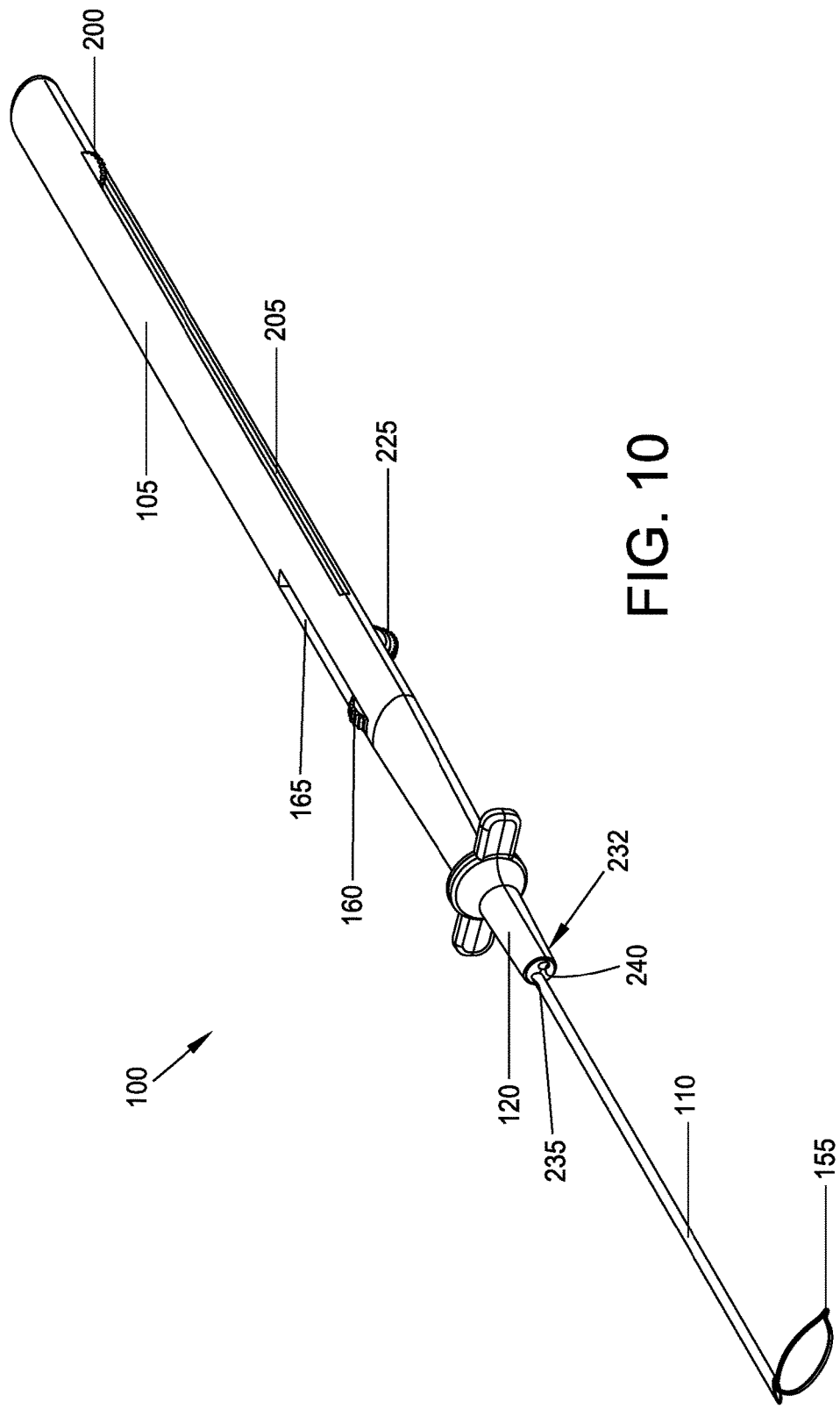
Figure 11:
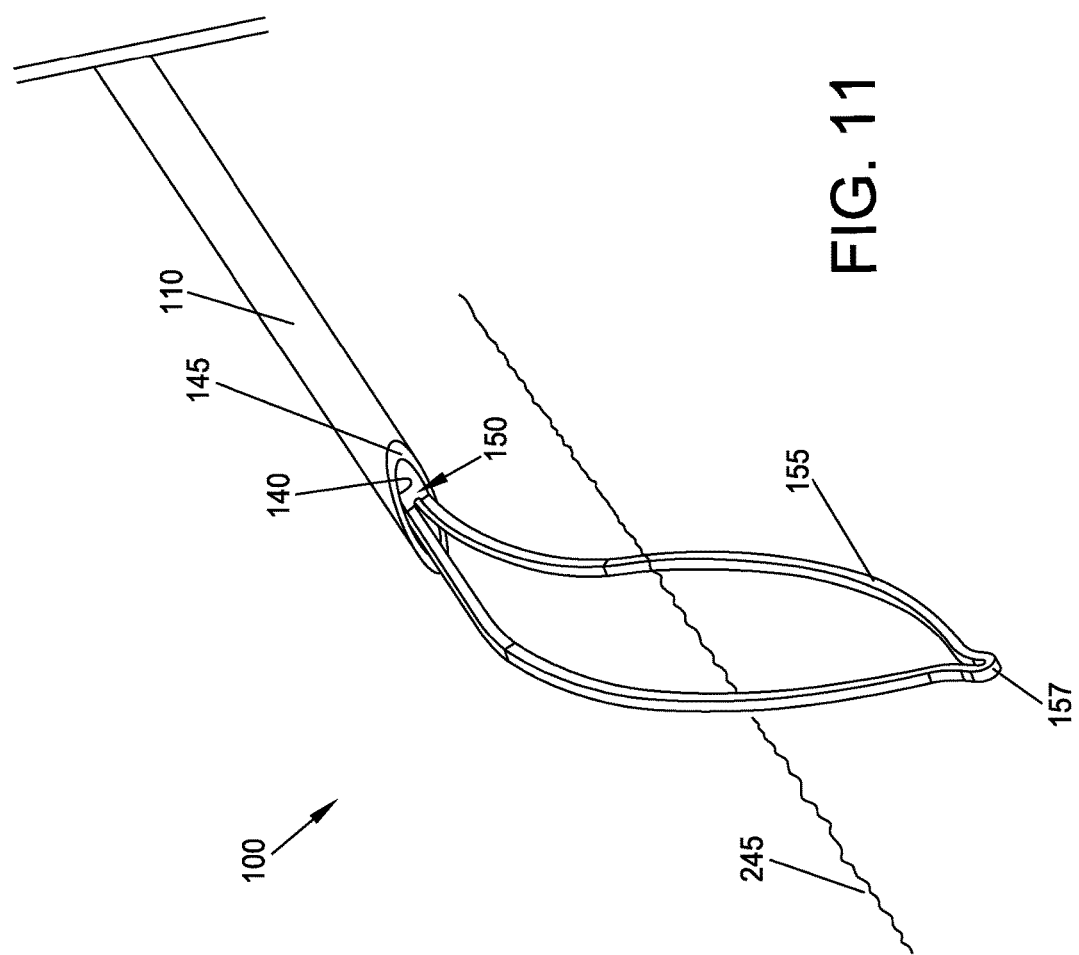

Suture needle 115 comprises a shaft 170 having a distal end 175, a proximal end 180 and a lumen 185 (FIG. 16) extending therethrough. Distal end 175 of suture needle 115 terminates in a sharp distal tip 190. Proximal end 180 of suture needle 115 is mounted to a suture needle mounting carriage 195 which is movably mounted within handle 105. A suture needle knob 200 is secured to suture needle mounting carriage 195. Suture needle knob 200 rides in a suture needle knob slot 205 formed in handle 105. On account of the foregoing construction, distal movement of suture needle knob 200 in suture needle knob slot 205 causes suture needle mounting carriage 195 to move distally within handle 105, whereby to move suture needle 115 distally relative to handle 105 (FIGS. 5 and 12-16), and proximal movement of suture needle knob 200 in suture needle knob slot 205 causes suture needle mounting carriage 195 to move proximally in handle 105, whereby to move suture needle 115 proximally relative to handle 105 (FIGS. 9-11). Note that when suture needle knob 200 is moved fully distal in suture needle knob slot 205, sharp distal tip 190 of suture needle 115 is substantially aligned with sharp distal tip 145 of retrieving needle 110 (FIGS. 5 and 13-16). Note also that when suture needle knob 200 is moved fully distal in suture needle knob slot 205, suture needle 115 is releasably locked in its fully distal position by a spring-loaded locking feature 207 which is mounted to slidable suture needle mounting carriage 195 and releasably interacts with adjacent portions of handle 105 (spring-loaded locking feature 207 is released from its locking engagement with adjacent portions of handle 105 by pressing inwardly on suture needle knob 200, against the power of its associated spring). A suture feed funnel 210 formed in the proximal end of handle 105 allows a securing suture 215 to be advanced distally through suture feed funnel 210 and into lumen 185 (FIG. 16) of suture needle 115.

Suture needle 115 comprises an arc-shaped cut-away 220 formed intermediate its length. A suture feed knob 225 is aligned with arc-shaped cut-away 220 in suture needle 115, but suture feed knob 225 is spring-biased away from arc-shaped cut-away 220 by a spring 230. The power of spring 230 may be overcome by the thumb or finger of a surgeon so as to force suture feed knob 225 through arc-shaped cut-away 220 and into lumen 185 of suture needle 115, whereby to allow a surgeon to use rotation of suture feed knob 225 to manually urge securing suture 215 distally within suture needle 115.

Retrieving needle 110 and suture needle 115 are configured (e.g., bent) so that when suture needle 115 is in its distal position and nose cone 120 abuts handle 105 (FIGS. 13-16), the sharp distal tips 145, 190 of retrieving needle 110 and suture needle 115 diverge from one another. In one preferred form of the invention, when suture needle 115 is in its distal position and nose cone 120 abuts handle 105 (FIGS. 13-16), the sharp distal tips of retrieving needle 110 and suture needle 115 are positioned approximately 10 mm apart from one another.

Nose cone 120 is movably mounted on retrieving needle 110 and suture needle 115. More particularly, nose cone 120 comprises a distal tip 232 (FIGS. 9, 10 and 12), a lumen 235 (FIGS. 10 and 12) for slidably receiving retrieving needle 110 and a lumen 240 (FIGS. 10 and 12) for slidably receiving suture needle 115. Lumen 235 and lumen 240 are disposed parallel to one another. In one preferred form of the invention, lumen 235 and lumen 240 are disposed so that their outermost walls are set approximately 3 mm apart. On account of the foregoing construction, when suture needle 115 is in its distal position and nose cone 120 is moved distally (FIG. 12), retrieving needle 110 and suture needle 115 can be forced into a substantially parallel configuration; and when suture needle 115 is in its distal position and nose cone 120 is moved proximally, e.g., into engagement with handle 105, retrieving needle 110 and suture needle 105 can assume their aforementioned diverging configuration (FIGS. 13-16).

In one preferred form of the invention, suture passer 100 is packaged and shipped with its suture needle 115 in its distal position, with retrieving loop 155 retracted into the interior of retrieving needle 110, and with nose cone 120 moved distally (FIG. 12), so that nose cone 120 shields the sharp distal tips 145, 190 of needles 110, 115 from accidental contact with medical personnel.

The suture passer of the present invention may be advantageously used with at least the following two modes of operation (although other modes of operation are also contemplated).

First Mode of Operation

The first mode of operation relates to suture retrieval (e.g., retrieval of the positioning suture), and will sometimes hereinafter be referred to as "the suture retrieving mode".

In this form of the invention, under the direct observation of an endoscope which has been previously inserted into the insulflated abdominal cavity, an appropriately-sized sheet of hernia mesh, which is presented in a rolled-up condition, is inserted into the abdominal cavity, whereupon the roll of hernia mesh is unrolled and centered on the hernia defect. The unrolled hernia mesh has been previously prepared for preliminary anchoring in this position by providing positioning sutures 245 that are secured to each corner of the hernia mesh.

Suture passer 100 is prepared for the retrieval of the positioning sutures 245 (FIG. 11) by placing it into the configuration shown in FIG. 9, i.e., suture needle 115 (not shown in FIG. 9) is withdrawn into handle 105 by sliding suture needle knob 200 proximally in its suture needle slot 205, and by sliding nose cone 120 proximally into engagement with handle 105. At this point, retrieving loop 155 (not shown in FIG. 9) is retracted into retrieving needle 110.

With suture passer 100 in this configuration, retrieving needle 110 is inserted, antegrade, through the abdominal wall, through the hernia mesh, and into the abdominal cavity. Then pre-formed retrieving loop 155 is extended from retrieving needle 110 as shown in FIG. 10, i.e., by sliding retrieving knob 160 forward (i.e., distally) in its retrieving knot slot 165. Retrieving loop 155 is positioned in a manner that allows the retrieving loop to "lasso" the free end of a positioning suture 245 (FIG. 11). To facilitate retrieval, retrieving loop 155 is fabricated from a metal (e.g., superelastic Nitinol) ribbon and constrained rotationally within retrieving needle 110, such that a pre-formed bend in the metal ribbon consistently positions the retrieving loop 155 at an angle generally normal to the sharpening plane of the sharp distal tip 145 of retrieving needle 110, as shown in FIG. 11. The metal ribbon is preferably further split and formed into the looped-shape shown in FIG. 11, with care being taken to provide a generous radius at the loop end 157 which mitigates stress cracking during repeated flexing throughout the repair procedure and which provides a shape detail into which the positioning suture 245 can be secured.

With positioning suture 245 disposed in retrieving loop 155, retrieving knob 160 is moved proximally in retrieving knob slot 165 so that retrieving loop 155 is withdrawn into retrieving needle 110, whereby to bind the positioning suture 245 to suture passer 100. Suture passer 100 is then used to pull the positioning suture 245 back through the hernia mesh and the abdominal wall. The positioning suture 245 is then released from the suture passer 100.

Second Mode of Operation

The second mode of operation relates to suture passing (e.g., passing a securing suture 215), and will sometimes hereinafter be referred to as "the suture passing mode".

In this form of the invention, under the direct observation of an endoscope that has been previously inserted into the insulflated abdominal cavity, the hernia mesh is placed approximately centered on the defect by the positioning sutures 245 previously defined. To secure the hernia mesh in place, additional sutures (i.e., securing sutures 215) are placed equidistant around the periphery of the hernia mesh, and placed in other positions that require additional securement as identified by the surgeon. These securing sutures 215 are required to mechanically secure the hernia mesh against movement resulting from the body motions that are expected during the first few weeks after surgery. After that, the peritoneum tissue (a lining in the abdominal cavity) grows into the porous hernia mesh substrate at the beginning of the healing process until the in-grown tissue is sufficient in strength to hold the hernia mesh in position as the healing process is completed.

To place a securing suture 215, the surgeon first approximates the location by making a small (e.g., 3 mm) incision on the abdomen skin. Then the suture passer 100 is used to deploy a securing suture through the incision. More particularly, the suture passer 100 is initially in the configuration shown in FIG. 12, i.e., suture needle 115 is fully distally extended so that suture needle 115 extends alongside retrieving needle 110 (suture needle 115 is releasably locked in its full-forward axial position by spring-loaded locking feature 207 which is mounted to slidable suture needle mounting carriage 195) and sharp distal tips 145, 190 of two needles 110, 115 are safely covered by sliding nose cone 120.

Figure 13:
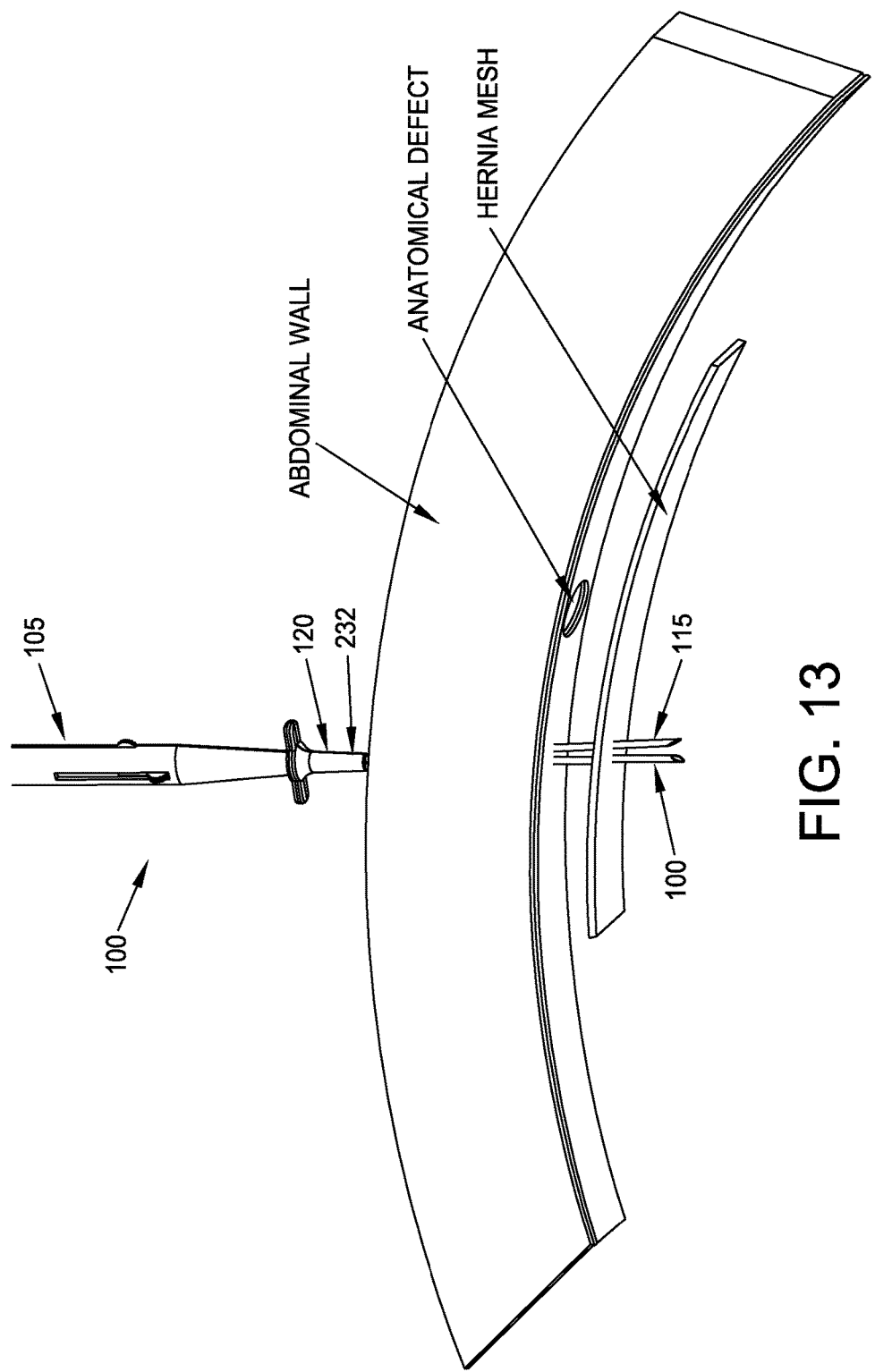
Figure 14:
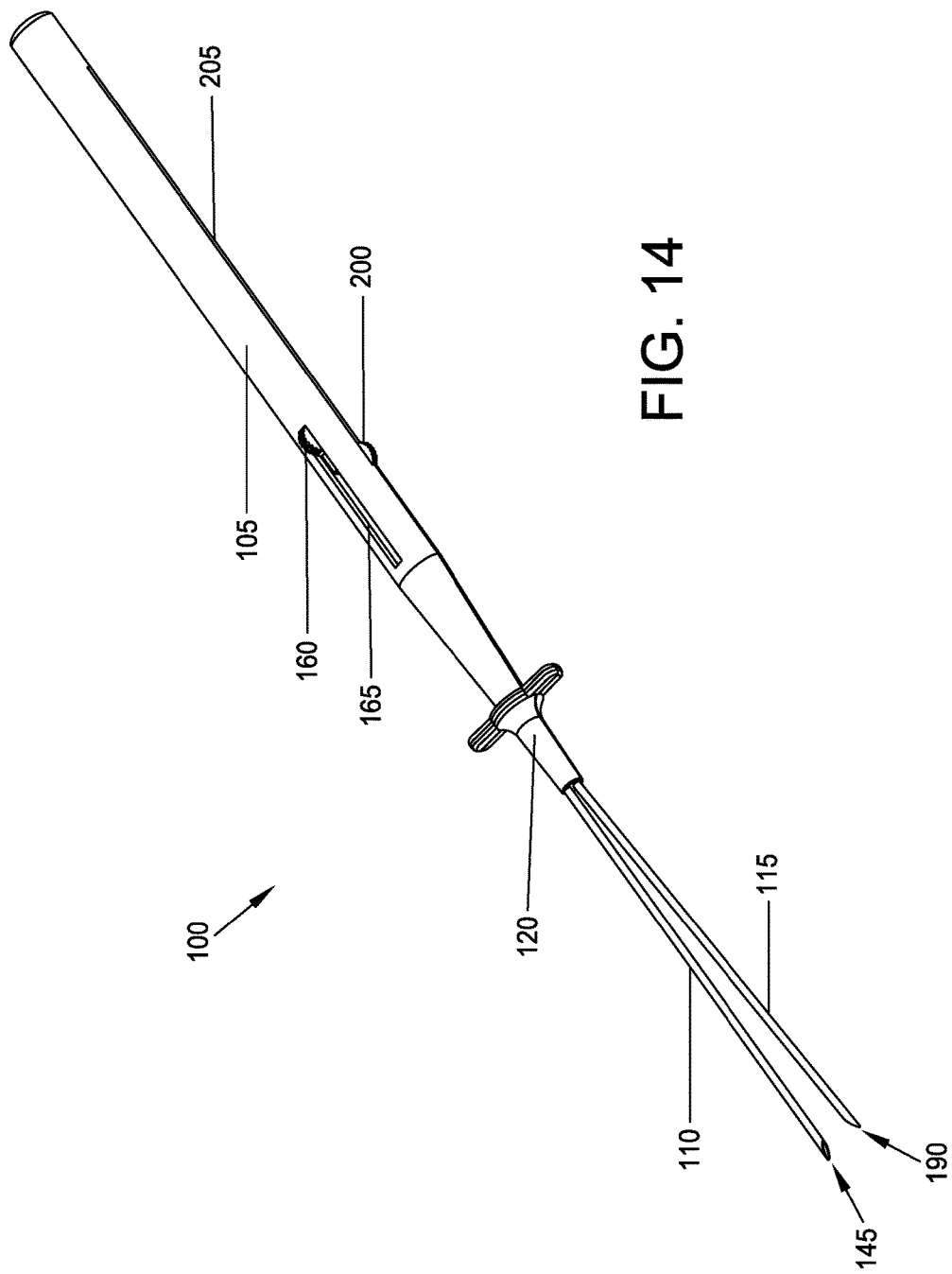

The distal tip 232 of nose cone 120 is positioned into the small (e.g., 3 mm) incision in the abdominal skin. While supporting the nose cone 120 axially, the surgeon then uses handle 105 to drive both needles 110, 115 forward through the abdominal wall (including the tough fascia layers and the healing perineum lining), through the hernia mesh and into the abdominal cavity under the direct view of the endoscope (FIG. 13). As the two needles 110, 115 extend distally out of nose cone 120, their pre-bent shape causes the spacing between the two needle tips 145, 190 to diverge from an entry spacing of approximately 3 mm to an expanded spacing of approximately 10 mm, as shown in FIG. 14. Significantly, this divergence of the two needles 110, 115 allows the securing suture 215 to secure multiple strands of the hernia mesh with a single pass of the securing suture, which reduces the possibility of pullout of the securing suture 215 through the hernia mesh during recovery. At the same time, this is done through a small (e.g., 3 mm) sub-dermal incision in the abdominal wall that can be stitched closed with good cosmetic results.

Figure 8:
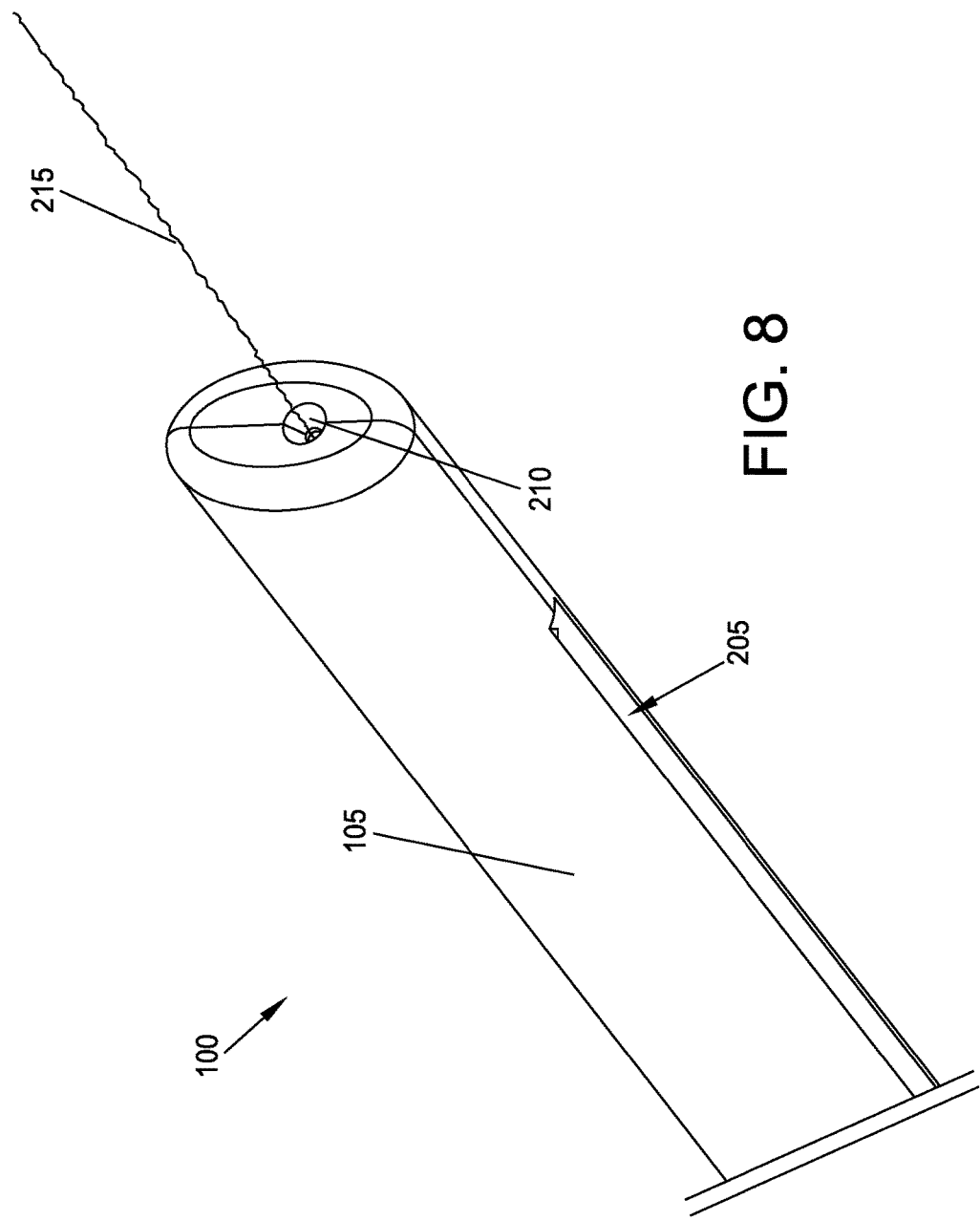
Figure 15:
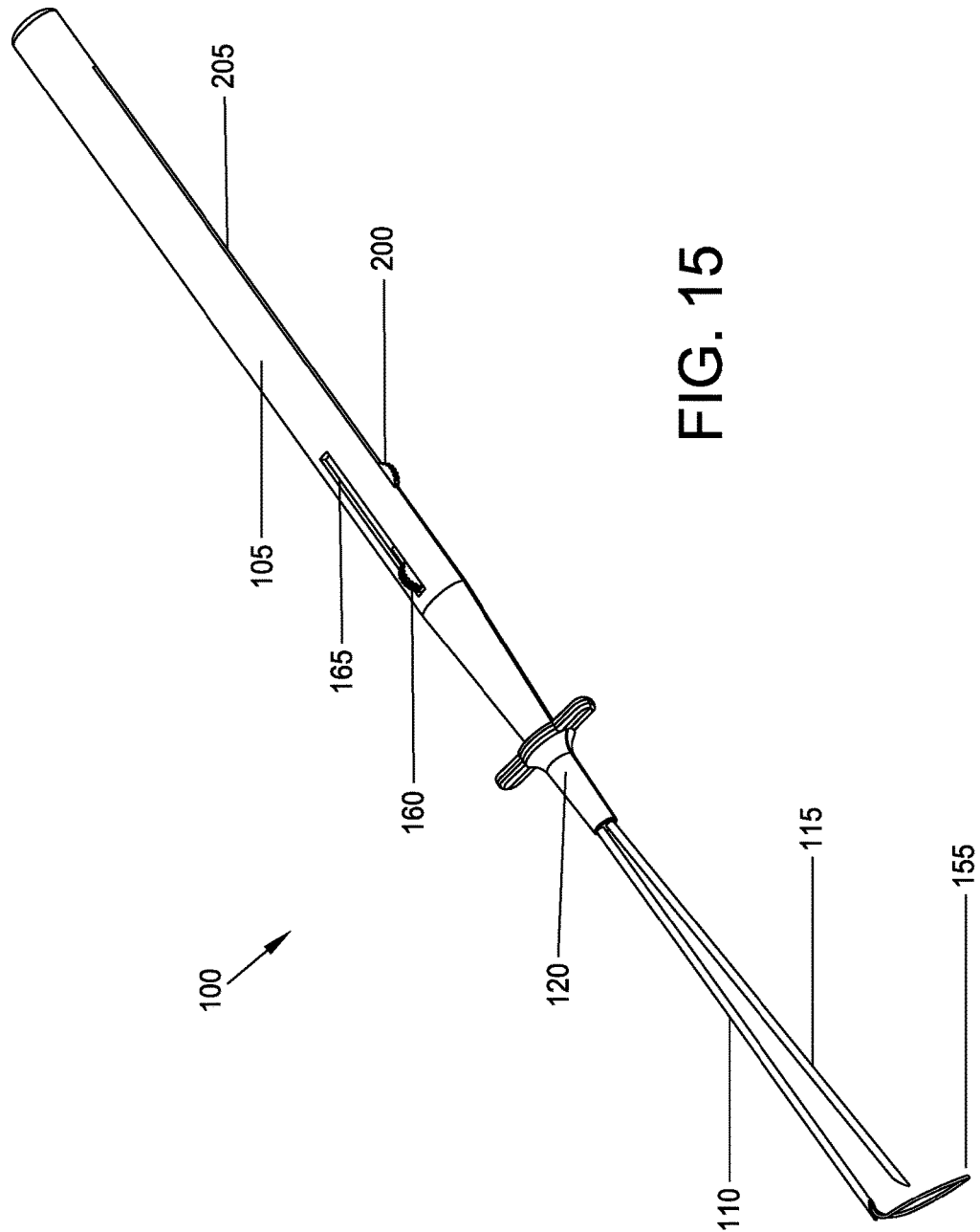

In preparation for passing the securing suture 215 through the abdominal wall, through the hernia mesh and back through the abdominal wall, retrieving loop 155 is then extended out of retrieving needle 110 by sliding retrieving knob 160 distally as shown in FIG. 15. The pre-bent shape of retrieving loop 155 positions the approximate center of retrieving loop 155 so as to be directly in line with the longitudinal axis of suture needle 115. The first end of securing suture 215 is then inserted into the suture feed funnel 210 in the proximal end of handle 105 as shown in FIG. 8 until the securing suture 215 is just short of the distal tip 190 of suture needle 115. Note that at this point in the procedure, securing suture 215 passes easily along the interior of suture needle 115 inasmuch as suture feed knob 225 is spring-biased away from arc-shaped cut-away 220 via spring 230.

Figure 16:
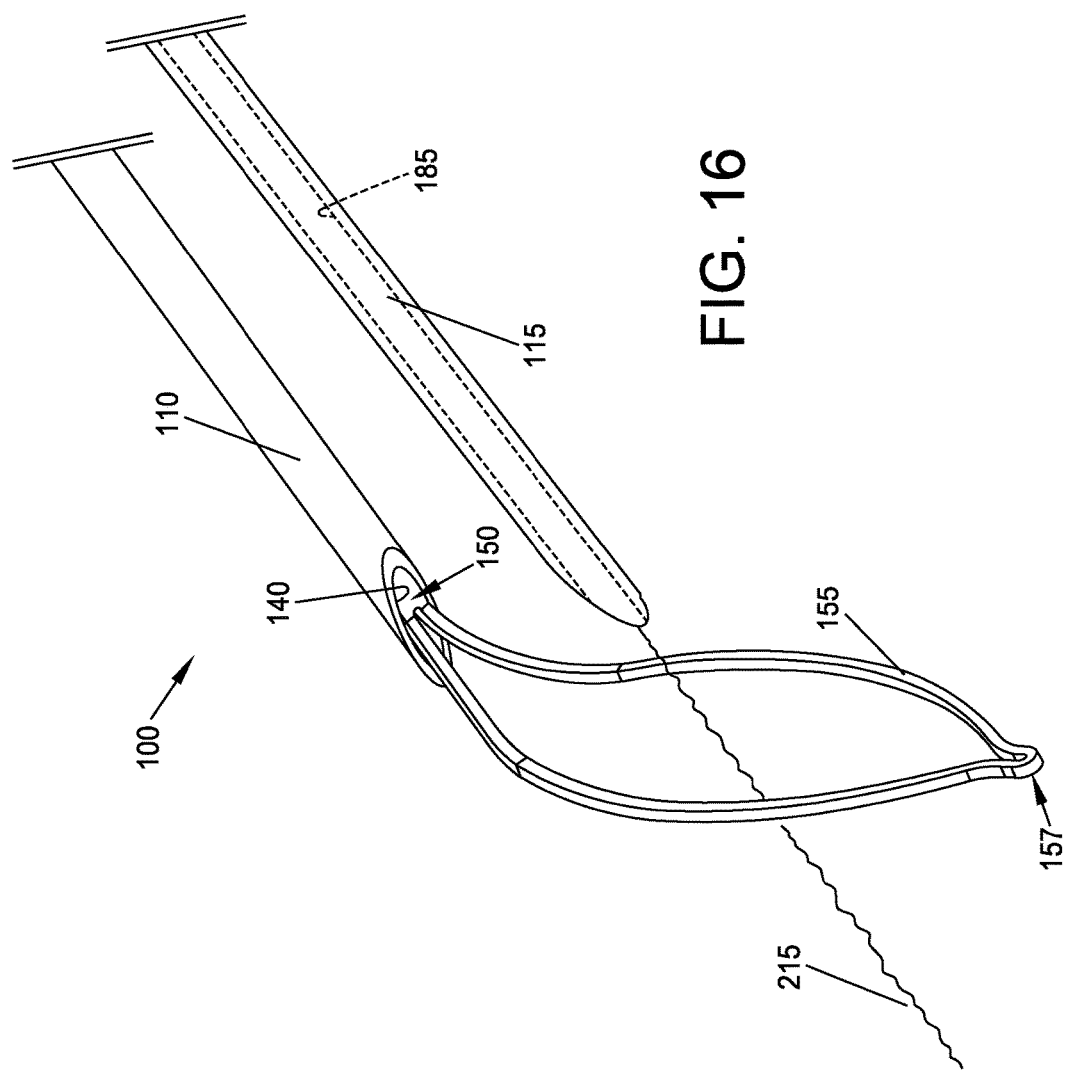

The securing suture 215 can then be fed forward through retrieving loop 155 using suture feed knob 225 as shown in FIG. 16. More particularly, securing suture 215 may be fed distally when suture feed knob 225 is depressed against the power of spring 230 (that pre-loads suture feed knob 225 into a normally non-contacting position) until the suture feed knob 225 extends through arc-shaped cut-away 220 and firmly contacts the securing suture loaded in suture needle 115. When suture feed knob 225 is thereafter rolled, securing suture 215 is driven forward within lumen 185 of suture needle 115 until securing suture 215 extends through retrieving loop 155 (FIG. 16). When suture feed knob 225 is released, the suture feed knob 225 returns to its normally non-contacting position relative to securing suture 215 and the securing suture is then free to slide in suture needle 115.

Retrieving loop 155, with securing suture 215 passing therethrough, is then withdrawn into retrieving needle 110 by retracting retrieving knob 160 in retrieving knob slot 165. At this point the securing suture 215 is secured to the suture passer 100.

Finally, with nose cone 120 held by hand against axial movement, handle 105 is withdrawn proximally. This action causes the first end of securing suture 215 to be pulled from the abdominal cavity to the space outside the body. Once the first end of the securing suture 215 is in the space outside the body, the first end of the securing suture 215 can be released from the suture passer 100 by sliding retrieving knob 160 forward (i.e., distally) so that retrieving loop 155 once again projects out of suture needle 115, whereupon the first end of the securing suture 215 can be removed from retrieving loop 155. At this point, the first end of the securing suture 215 is tied to the second end of the securing suture, completing the anchoring process.

It should be appreciated that as retrieving loop 155 is pulled back within retrieving needle 110, the securing suture 215 is secured against the flat of the needle tip 145. It should also be appreciated that when both needles 110, 115 are withdrawn from the abdominal cavity, the securing suture 215 is pulled taut against the hernia mesh and the abdominal wall and then released. The surgeon now has both ends of a securing suture 215 that is ready to be tied off, with the knot being sub-dermally positioned into the incision. It should be noted that the insertion incision is as small as possible for healing and cosmetic reasons, and the two needles 110, 115 must enter the abdomen spaced apart about 3 mm so as to be contained in the incision. However, the two needles must also spread out to about 10 mm as they pass through the hernia mesh in order to secure multiple strands of the hernia mesh for strength and resistance to pull-out.

Alternative Configuration

Figure 12:
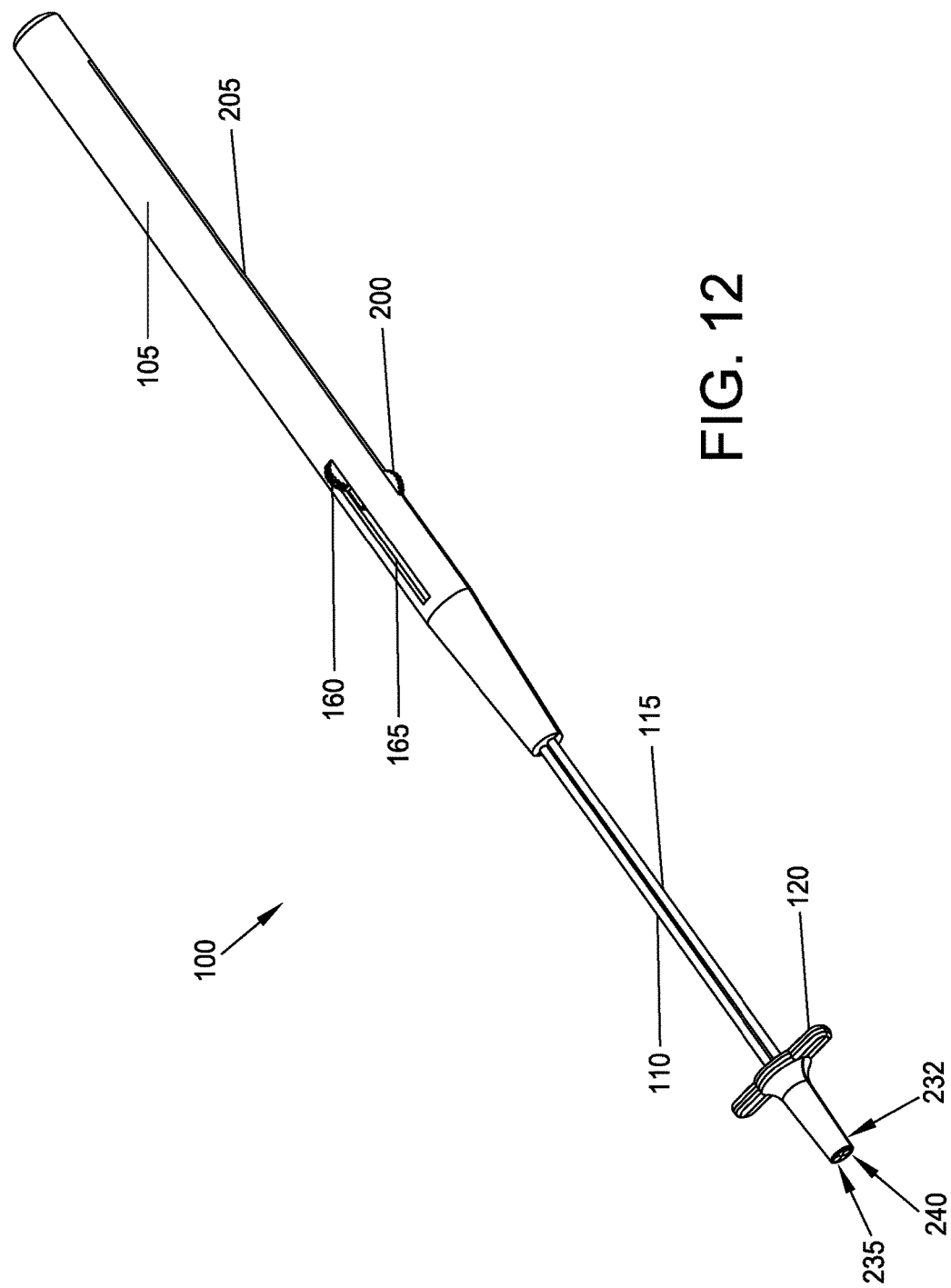
FIGS. 12-16 are schematic views showing the novel suture passer of FIGS. 5-8 being used to pass and retrieve a securing suture.
Figure 17:
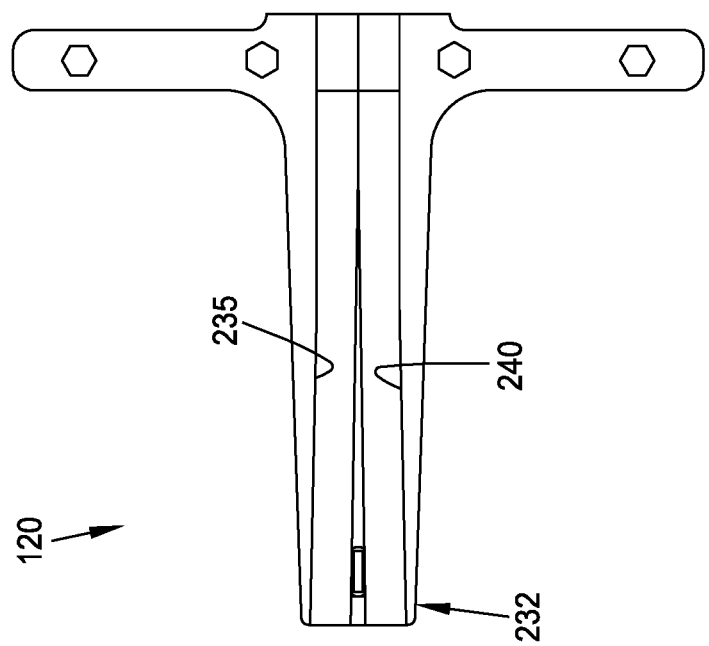
FIG. 17 is a schematic view showing an alternative form of nose cone for use with the novel suture passer of the present invention.

In the foregoing disclosure, needles 110, 115 are characterized as being pre-bent so as to flair outward to a spread of approximately 10 mm (FIGS. 13-16) when the needles are in an unconstrained condition, and sliding nose cone 120 is characterized as having two parallel lumens 235, 240 so as to selectively constrain the two needles 110, 115 to a spread of approximately 3 mm (FIGS. 5 and 12). However, if desired, other approaches may be used to cause needles 110, 115 to flair outward as they pass through nose cone 120 and into the abdominal wall and hernia mesh. By way of example but not limitation, needles 110, 115 may be formed with a straight configuration, and lumens 235, 240 in nose cone 120 may be formed with a diverging configuration (e.g., in the manner shown in FIG. 17), so that needles 110, 115 will flair outward as they pass through nose cone 120 (e.g., from a spread of approximately 3 mm at nose cone 120 to a spread of approximately 10 mm at the surgical mesh).

Applications Other than Hernia Repair

In the foregoing description, suture passer 100 is discussed in the context of its use in a hernia repair procedure. However, it should be appreciated that suture passer 100 may be used in other types of procedures as well, e.g., for laparoscopic suturing, for arthroscopic suturing, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A suture passer configured to pass suture through at least one object, the suture passer comprising:
a handle, the handle comprising a first handle lumen and a second handle lumen, the first handle lumen defining a first handle lumen axis and the second handle lumen defining a second handle lumen axis, the second handle lumen axis being disposed parallel to the first handle lumen axis;
a first needle comprising a distal end, a proximal end and a first needle lumen extending therebetween, the proximal end of the first needle being disposed within the first handle lumen of the handle, with the first needle being fixedly mounted to the handle;
a retrieving loop selectively extendable out of, and selectively retractable into, the first needle lumen of the first needle;
a second needle comprising a distal end, a proximal end and a second needle lumen extending therebetween, the proximal end of the second needle being disposed in the second handle lumen of the handle, with the second needle being slidably mounted to the handle so as to be movable between a first position wherein the distal end of the second needle is disposed within the handle, and a second position wherein the distal end of the second needle extends out of the handle; and
a nose cone, the nose cone comprising a first nose cone lumen having a distal end and a proximal end and a second nose cone lumen having a distal end and a proximal end, the first nose cone lumen defining a first nose cone lumen axis extending between the distal end of the first nose cone lumen and the proximal end of the first nose cone lumen, and the second nose cone lumen defining a second nose cone lumen axis extending between the distal end of the second nose cone lumen and the proximal end of the second nose cone lumen, the first nose cone lumen being sized to slidably receive the first needle and the second nose cone lumen being sized to slidably receive the second needle, and the second nose cone lumen axis being disposed at an angle relative to the first nose cone lumen axis, such that the distance between the distal end of the first nose cone lumen and the distal end of the second nose cone lumen is greater than the distance between the proximal end of the first nose cone lumen and the proximal end of the second nose cone lumen;
wherein the first handle lumen and the second handle lumen are separated by a first distance, and further wherein the proximal end of the first nose cone lumen and the proximal end of the second nose cone lumen are separated by the first distance and the distal end of the first nose cone lumen and the distal end of the second nose cone lumen are separated by a second, larger distance, such that when the second needle is in the second position and the nose cone is moved distally along the needles so that the distal ends of the first needle and the second needle are disposed within the distal ends of the first nose cone lumen and the second nose cone lumen, respectively, the distal ends of the first needle and the second needle are laterally constrained so as to be separated by the second distance, and when the nose cone is moved proximally along the needles so as to uncover the distal ends of the first needle and the second needle, the distal ends of the first needle and second needle diverge laterally such that the distal ends of the first needle and the second needle are separated by a third distance; and wherein the second distance is greater than the first distance and the third distance is greater than the second distance.

2. A suture passer according to claim 1 wherein the at least one object comprises tissue.

3. A suture passer according to claim 1 wherein the at least one object comprises hernia mesh.

4. A suture passer according to claim 1 wherein the at least one object comprises tissue and hernia mesh.

5. A suture passer according to claim 1 wherein both of the first and second needles are pre-bent so that when the second needle is in the second position, and the nose cone is moved proximally so as to uncover the distal ends of the first needle and the second needle, the tips of the first needle and the second needle are separated by a fourth distance, and further wherein the fourth distance is greater than the third distance.

6. A suture passer according to claim 1 wherein the first and second needles are mounted to the handle, and further wherein the nose cone is movable relative to the handle.

7. A suture passer according to claim 6 wherein the nose cone is configured to be disposable over the distal ends of the first and second needles until the distal ends of the first and second needles are penetrating the object.

8. A suture passer according to claim 1 wherein the retrieving loop comprises a pre-bent ribbon of a superelastic shape memory material that is disposed at cross-angles with, and concentric to, the distal end of the first needle when the retrieving loop is selectively slidably extended from the first needle.

9. A suture passer according to claim 1 wherein the first distance is approximately 3 mm and the third distance is approximately 10 mm.

* * * * *